United States Patent [19]

Hseih et al.

[11] Patent Number: 5,545,155
[45] Date of Patent: Aug. 13, 1996

[54] ABSORBENT ARTICLE WITH PLATES

[75] Inventors: Tong-Ho Hseih, Marlboro; Theodore A. Foley, East Brunswick; Anthony N. Marascio, New Brunswick, all of N.J.

[73] Assignee: McNeil-PPC, Inc., Milltown, N.J.

[21] Appl. No.: 220,073

[22] Filed: Mar. 30, 1994

[51] Int. Cl.⁶ .................... A61F 13/15; A61F 13/20
[52] U.S. Cl. ............. 604/378; 604/358; 604/383; 604/385.1
[58] Field of Search ................. 604/358, 369, 604/371, 378, 383, 385.1

[56] References Cited

U.S. PATENT DOCUMENTS

| | | | |
|---|---|---|---|
| 2,896,618 | 7/1959 | Schaefer | 604/378 |
| 3,749,627 | 7/1973 | Jones . | |
| 3,945,386 | 3/1976 | Anczurowski et al. | 604/383 |
| 4,282,874 | 8/1981 | Mesek | 604/383 |
| 4,321,924 | 9/1982 | Ahr | 604/385.1 |
| 5,143,779 | 9/1992 | Newkirk et al. . | |
| 5,387,209 | 7/1995 | Yamamoto et al. | 604/370 |

FOREIGN PATENT DOCUMENTS

| | | | |
|---|---|---|---|
| 4161154 | 6/1992 | Japan | 604/378 |
| 9014815 | 12/1990 | WIPO | 604/378 |
| 9309741 | 5/1993 | WIPO | 604/378 |

Primary Examiner—Mary Beth Jones
Assistant Examiner—P. Zuttarelli
Attorney, Agent, or Firm—James P. Barr

[57] ABSTRACT

An absorbent article is provided which is capable of rapidly absorbing gushes of menstrual fluid, comprising an upper plate and a lower plate which are spaced apart from each other, and wherein a plurality of openings extend through the upper plate. The openings are large enough to allow easy passage of the fluid to the interior of the article and the plates are spaced apart to allow each flow of the fluid in the x–y plane.

19 Claims, 10 Drawing Sheets

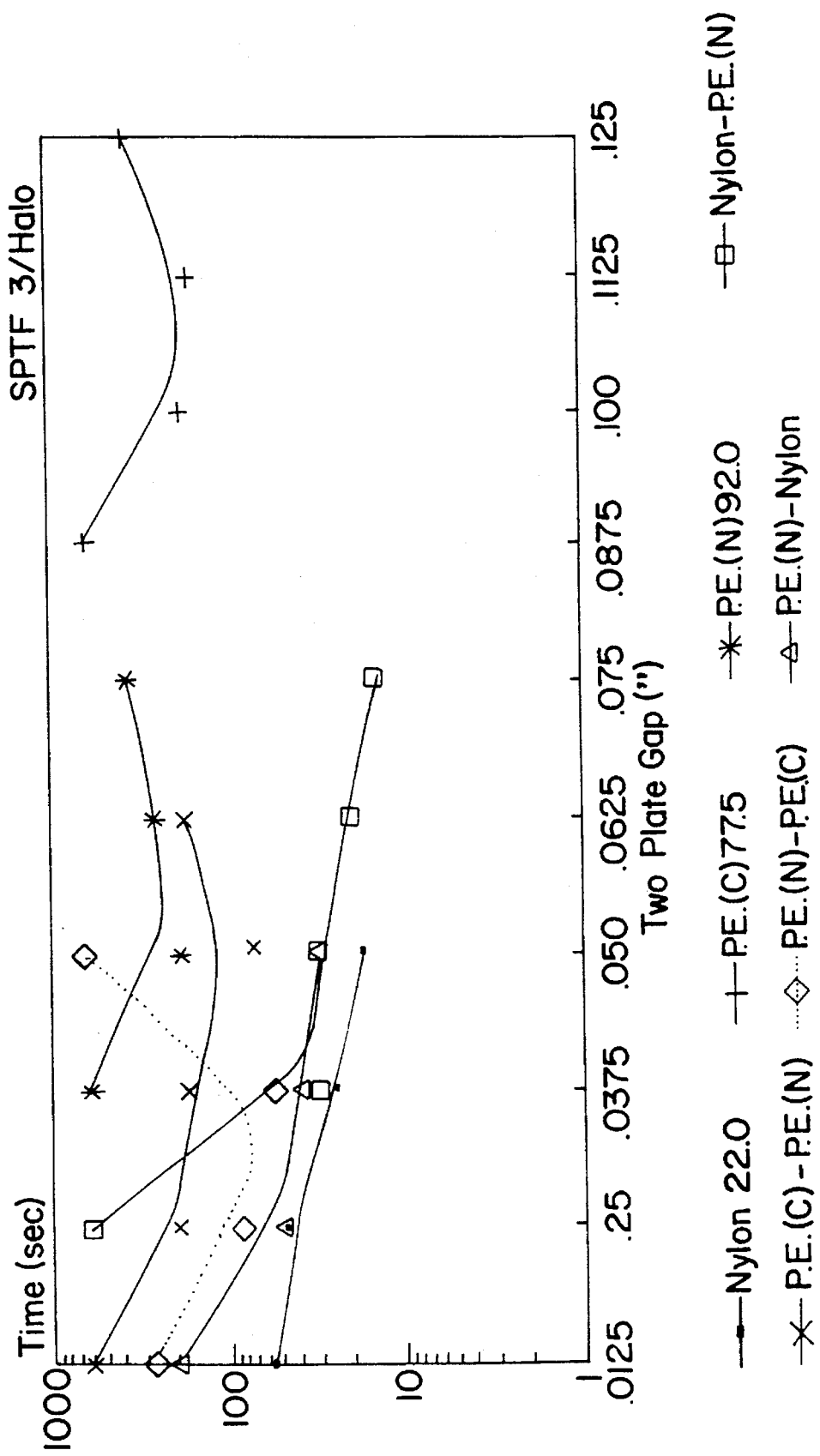

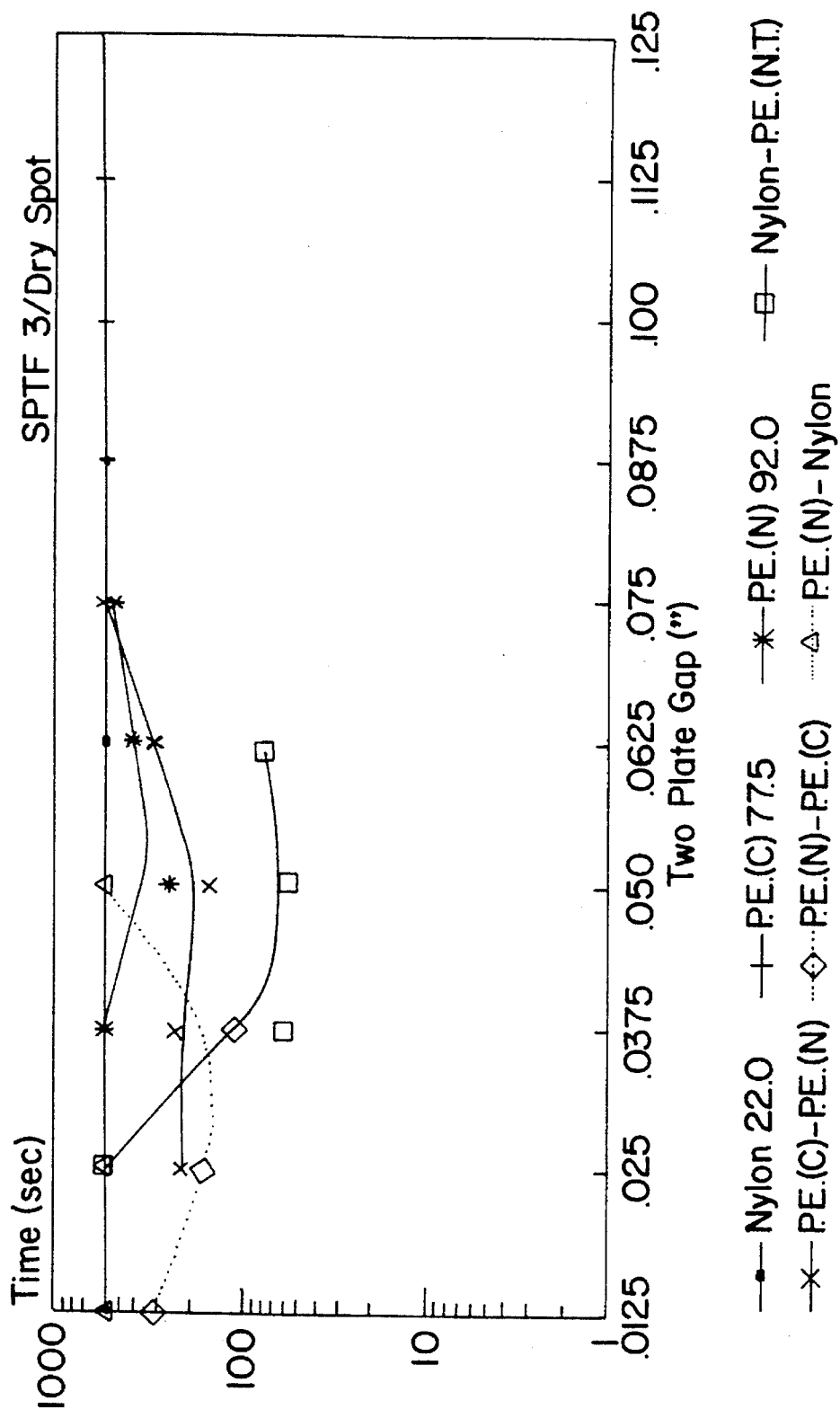

ABSORBENT ARTICLE WITH PLATES

BACKGROUND OF THE INVENTION

1. Field of the Invention

This invention relates to an absorbent article for absorbing body fluids such as menstrual fluid, vaginal discharge and/or urine. More particularly, this invention relates to an absorbent article that is particularly well suited for absorbing menstrual fluid that is discharged in gushes. The remainder of this specification will discuss application of this invention to absorb menses and other vaginal discharges. However, the teachings are equally applicable to incontinence products as well.

2. Prior Art

Conventional full-size sanitary protection products, and other feminine hygiene products such as adult incontinence devices, typically contain an absorbent element, a fluid-pervious body-contacting element and a fluid-impervious undergarment-facing element. The principle function of such articles is to absorb body fluid, such as menstrual fluid, from the wearer and retain the fluid in order to prevent the fluid from soiling the wearer's garments. Such products are designed primarily around the premise that, for example, menstrual discharges are constant and even with a relatively low average flow rate. Such products are also designed around the premise that menstrual fluid, specifically, is a low viscosity liquid that behaves much as water behaves when exposed to an absorbent fibrous material. Thus, the materials of sanitary protection products typically used in products today, although capable of absorbing relatively large quantities of low viscosity fluid, tend to absorb such fluid at relatively slow rates. More viscous fluid are absorbed even more slowly or sometimes not at all. Thus, theoretically, sanitary napkins have the capability of absorbing between 50 and 100 grams of fluid. However, soiling may occur after only 5 to 10 grams of fluid are deposited on the absorbent article. Two of the primary reasons why soiling occurs is that conventional napkins do not have the ability to absorb fluid that is discharged at a high flow rate, and they are designed to absorb fluid that behaves like water rather than a fluid containing 85% solids.

It is commonly known that menstrual fluid is composed of blood that comes from the blood vessels of a woman's endometrium. It is also known that menstrual further contains fragments of endometrial tissue, mucus from the vagina and cervix, minerals, and protein. It is thicker and darker red-brown than blood from a vein and is about 85% solids and 15% water. Solids include endometrial tissue and red and white blood cells which together form aggregates that are commonly referred to as "clots." Menstrual fluid is highly viscoelastic with viscosity decreasing only upon the application of shear, such as that applied between a woman and a sanitary napkin.

It is also commonly known that about 76% of the menstrual flow occurs during the first three days of menses, with the most profuse bleeding occurring on the second day. During this time, menstrual fluid is often discharged in gushes that can total approximately 4 cc of fluid in a matter of seconds. This often occurs in the morning, just after awakening. During the night, and depending on the position one assumes during sleep, menstrual fluid can collect in the vagina. Upon standing, this fluid will then exit the vagina at a relatively fast flow rate. This phenomenon can also occur after sitting for long periods of time.

The main absorbent portion of conventional sanitary napkins comprise some material that has an ability to absorb a large quantity of a low viscosity fluid. The most prevalent material in use are wood pulp fluff and wood pulp fluff used in conjunction with sphagnum and superabsorbent polymers, where the latter is based primarily on acrylic acid. In the case of sphagnum, fluid is absorbed by a high capillary pressure which draws fluid into the capillary structure. In the case of a superabsorbent polymer, a concentration of fluid in the polymer is created. The fluid causes the polymer to swell, and as it swells it allows more fluid to be absorbed until its capacity is reached when it is fully swollen.

One problem exhibited by products using either sphagnum or superabsorbent polymer is that the time necessary for either sphagnum or superabsorbent polymers to absorb the fluid is many times longer than the short time during which a relatively large quantity of fluid is deposited on the napkin in a gush. As a consequence, the fluid will pool on the top of the napkin before it can be completely taken up by the absorbent material. If the fluid pools, there is very little that can contain it until it is absorbed. Therefore, the chances that the fluid will run off the napkin is very great.

Conventional products on the market, and the prior art upon which these products are based, try to overcome this inability to absorb gushes by interposing a transfer layer material between the cover and the absorbent core. The purpose of this transfer layer is to act as a fluid transfer buffer layer by quickly drawing fluid from the cover, to hold it until the absorbent core can take absorb it, and then to transfer it to the absorbent core. However, these products still depend on wicking into the cover, between the cover and transfer layer, and between the transfer layer and the core. The time needed for the fluid to rapidly and fully pass through the cover, to fully wick into the transfer layer, and then to wick into the core is still sorely insufficient to absorb a large gush. Therefore, the chances for failure remain. All of the components in this fluid transfer chain, starting with the cover and continuing on to the transfer layer and absorbent core, inhibit the rapid and complete transfer of large quantities of fluid. Further, such products have a close fibrous network, with ever decreasing pore size openings as one proceeds further into the thickness of the product, that increases capillary pressure and ability to wick low viscosity fluids such as water. Thus, what is obtained is a fibrous structure that can draw a fluid into it but restricts the absorption of solids such as those present in menstrual fluid.

The primary object of this invention is to overcome these deficiencies in the prior art.

SUMMARY OF THE INVENTION

This invention provides for an absorbent article capable of rapidly absorbing gushes of menstrual fluid, comprising an upper plate and a lower plate which are spaced apart from each other, and wherein a plurality of openings extend through the upper plate.

This invention also provides for an absorbent article capable of rapidly absorbing gushes of menstrual fluid, comprising an absorbent product comprising:

a fluid permeable cover layer;

an absorbent core;

a fluid impermeable barrier layer; and two plates, comprising an upper plate and a lower plate, positioned between the barrier layer and the absorbent core, wherein the upper plate is adjacent the absorbent core and the lower plate is adjacent the barrier layer, wherein the plates are spaced apart from each other, and wherein a plurality of openings extend through the upper plate.

BRIEF DESCRIPTION OF THE DRAWINGS

FIGS. 7–12 are graphical representation of the effect of gap distance on absorption time.

DETAILED DESCRIPTION OF THE INVENTION

Figure 1:
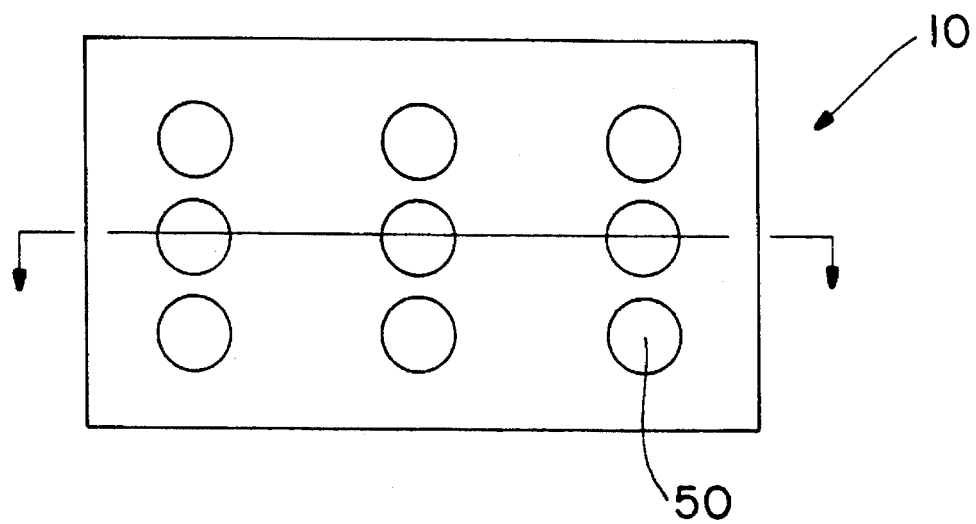
FIG. 1 shows an upper plan view of the plates of this invention.
Figure 2:
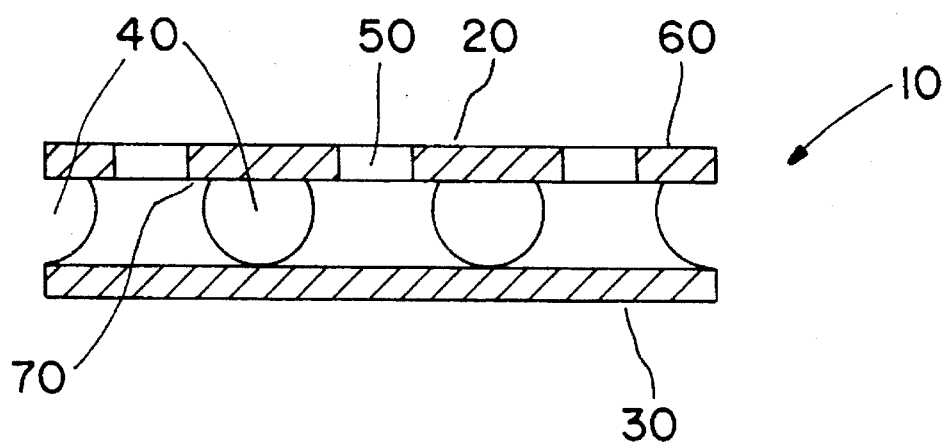
FIG. 2 shows a cross sectional view of the plates of this invention along line 2—2 of FIG. 1.

Referring to FIGS. 1 and 2, this invention calls for an absorbent product comprising a pair of sheets or plates 10 comprising an upper plate 20 and a lower plate 30. The upper and lower plates 20,30 are separated from each other by a space. In order to maintain that space, one or more spacer elements 40 can be inserted.

The plates 20,30 can be made of any hydrophobic or hydrophilic material. The thickness of each plate is not critical. However, it can preferably be selected from the range of from about 0.005 to about 0.050 inch. The materials of construction and the thickness of the plates should be designed so that they are resistant to wet collapse when exposed to fluid. Preferably, the plates are made from any smooth fibrous or nonfibrous material. Nylon or sheets coated with nylon have been found to be useful. Also found to be useful have been compressed fibrous sheets and sheets laminated with tissue paper. The thickness of plates made from nylon and from the fibrous tissue laminate discussed above is preferably in the range of from about 0.020 to 0.040 inch.

It is preferable that the surface of at least one of the plates 20,30 that are exposed to fluid be sufficiently wettable to provide a low contact angle, that is a contact angle of less than 90 degrees, when in contact with body fluid, so that the fluid will easily flow across their surface. In order to accomplish this, the materials of plates 20,30 can be chosen from those materials which are known in the art, such as nylon, cellulosics, polyvinyl alcohols, acrylics, etc., which have low energy surfaces. It is also possible and useful to coat materials with high energy surfaces with a surfactant in order to increase their wettability. Such surfactants are well known in the art. Other means of increasing wettability can also be used, such as by corona discharge treatment of, for example, polyethylene or polypropylene, or by caustic etching of, for example, polyester.

The spacer elements 40 can also be selected from any number of materials. Selection, however, should be based on the material's ability to withstand wet collapse when simultaneously subjected to compressive forces and fluid. Preferably, the spacer elements 40 are from a material such as polystyrene foam. Most preferably, the spacer elements are formed as an integral part of either the upper and/or lower plates 20,30. In FIG. 1, the spacer elements are shown as nubules extending from the bottom surface of the upper plate and resting on the top surface of the lower plate. However, they can be formed by means of any shaped and elevated embossments and corrugations.

In order to maintain stability against sliding of the plates with respect to each other and changing of the space between them, it is acceptable, and may be preferable, to apply adhesive between the spacer elements 40 and the upper and lower plates 20,30. Preferably, the adhesive is wettable.

Extending through the upper plate 20 are a plurality of openings 50. These openings 50 extend completely through the upper plate 20 and may but do not need to extend through the bottom plate 30. The purpose of the openings is to allow fluid that is deposited on the upper plate 20 to flow with as little restriction as possible into the space between the upper plate 20 and the lower plate 30. To accomplish this, it is necessary that the total surface area of the upper plate 20 taken up by the openings 50 be from about 0.01 to preferably about 8.00 square inches. More preferably, it will be from about 0.25 to about 2.0 square inches. Having this much open area on the upper plate 20 will allow fluid that is deposited on the upper plate to easily flow into the open space below.

Looking at any individual opening 50, it is preferable that it be large enough to easily pass any nonabsorbable material, such as clots, that are contained in the fluid. Thus, it is preferable that the opening 50, assuming that it is circular, be at least about 0.020 inches in diameter. More preferably, the opening 50 size should be from about 0.05 to about 0.25 inches in diameter. It is important to note, however, that the geometry of the openings 50 is not important. What is important is that the opening 50 be sufficient to allow easy passage of nonabsorbable material. If the openings 50 are not circular, then the measurement should be made across the most narrow part of the opening 50 which would be most restrictive to the flow of nonabsorbable material.

Figure 3:
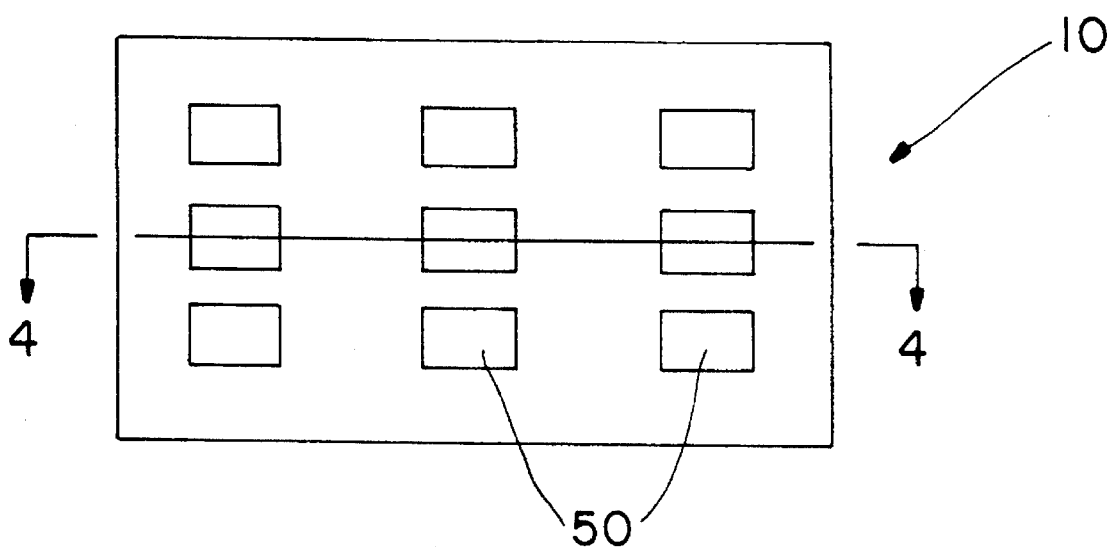
FIG. 3 shows an alternative design in plan view of the plates of this invention.
Figure 4:
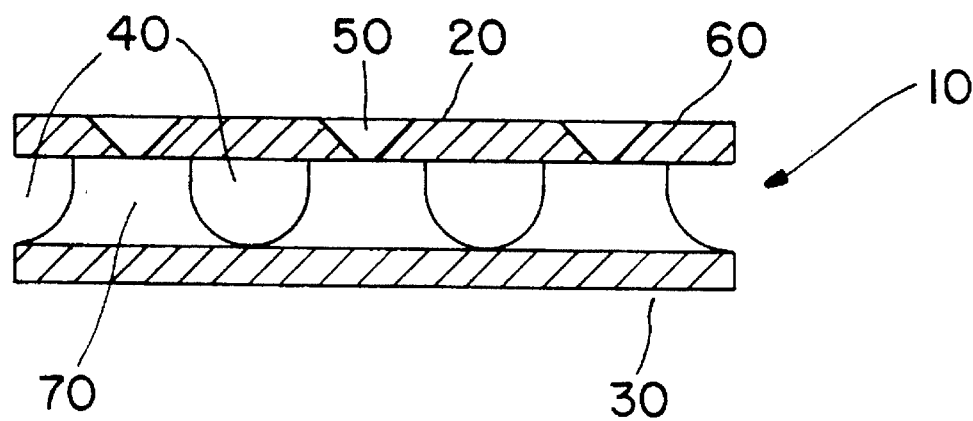
FIG. 4 shows a cross sectional view of an alternative view of this invention from line 4—4 of FIG. 3.

Looking at FIGS. 3 and 4, it is preferable that the openings 50 be funnel shaped. To explain this more fully, the upper layer 20 has a top surface 60 and a bottom surface 70. If the diameter of the opening 50 at the top surface 60 is greater than the diameter of the opening 50 at the bottom surface 70 (or, in the case where the opening is not circular, the area of the opening at the top surface 60 is greater than the area of the opening at the bottom surface 70) then fluid that flows into the space between the upper and lower plates 20,30 will be slightly restricted from flowing back toward the top surface 60.

Figure 6:
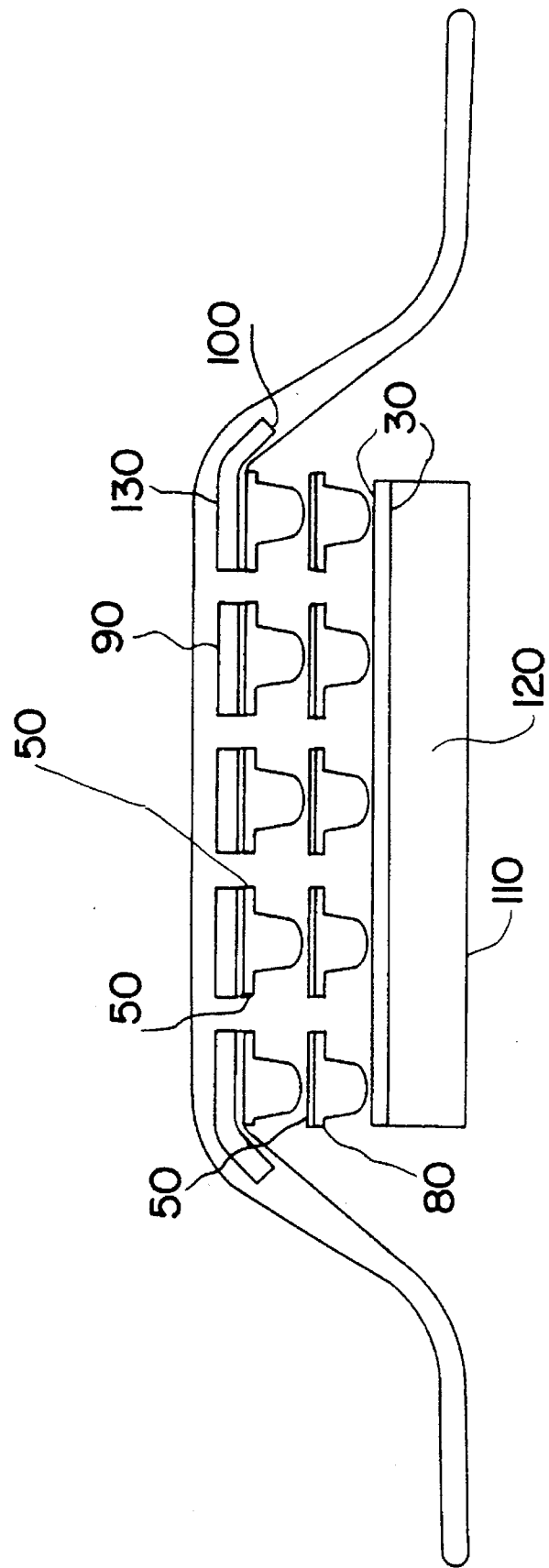
FIG. 6 shows a cross sectional view of the sanitary napkin of FIG. 5 along line 6—6.

Looking at FIG. 6, it is permissible, and in fact may be preferable, to place intermediate plates 80 with additional spacer elements 40 between the upper and lower plates 20,30. The intermediate plate 80 also contains openings 50 allowing easy passage of fluid to the open space between the plates.

Although not critical to the invention, it is recommended that the lower plate 30 contain no openings 50. Thus, when fluid flows downward in the z-direction from the upper plate 20 to the lower plate 30, the fluid will then flow laterally in the x,y-directions. As fluid is spread out in the x,y-directions, it can be more easily absorbed by other absorbent elements (which elements are more fully described below).

The upper, lower, and (optional) intermediate plates 20,30,80 described above are shown in the Figures as essentially planar sheets that are parallel to one another. However, they need not be planar or parallel. The only necessary feature be that the plates be spaced apart from each other. Further, the spacing between the plates need not be constant, but instead may change along the x,y-directions. Thus, products that have curved surfaces for improved body fit may have plates that are curved as well to maintain a gap between plates. Preferably, this gap is at least 0.0005 inch. More preferably, this gap is from about 0.025 inch to about 0.125 inch.

Figure 5:
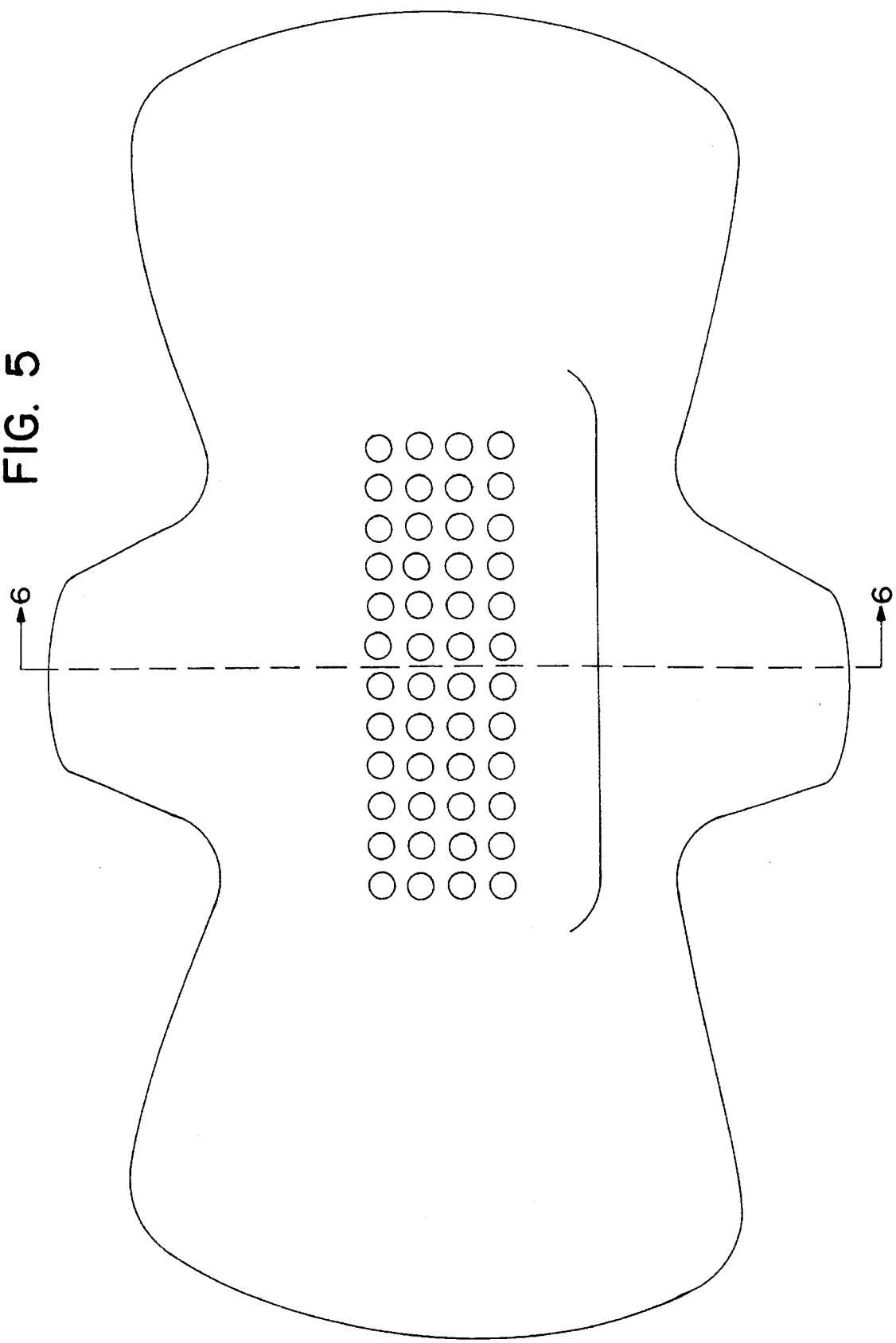
FIG. 5 shows a plan view of a sanitary napkin made according to this invention.

Referring to FIGS. 5 and 6, the upper, lower, and (optionally) intermediate plates 20,30,80 may be combined with other elements normally used in sanitary napkins to improve upon the ability of a sanitary napkin to absorb gushes. In a typical napkin, then, would be found a fluid permeable cover layer 90, an absorbent core 100, a fluid impermeable barrier layer 110. The upper and lower plates 20,30 are positioned between the barrier layer 110 and the absorbent core 100, wherein the upper plate 20 is adjacent the absorbent core 100 and the lower plate is adjacent the barrier layer 110. Optionally, an additional bulk layer 120 may be positioned between the barrier layer 110 and the lower plate 30.

The fluid permeable cover layer 90 may be composed of a woven or non-woven fibrous fabric or an apertured plastic sheet. The fibrous fabric may be composed of cellulosic fibers such as cotton or rayon, or it may be composed of thermoplastic fibers such as polypropylene or polyethylene. It may be chemical or thermoplastic binder bonded fabric, a needle punched bonded fabric, an entangled or modified-entangled fabric, a spunbond or meltblown fabric, or composites of these fabrics.

Apertured plastic covers are well-known in the art. The cover may be selected from sheets known as Dri-weave™ (U.S. Pat. No. 4,324,246), Reticulon® (U.S. Pat. No. 4,690,679) or Apex™ (U.S. patent application No. 07/744744) now abandoned, all herein incorporated by reference.

Additional fluid permeable cover layers from the prior art are absorbent, porous, dry-laid, nonwoven webs or scrim type materials such as those described by I.S. Ness in U.S. Pat. No. 4,880,419 and by Campau in U.S. Pat. No. 3,044,467, Hendricks in U.S. Pat. No. 3,463,154 and Sneider in U.S. Pat. No. 3,570,491 (herein incorporated by reference).

There are also fluid permeable cover layers of the prior art such as those described by T. J. Luceri in U.S. Pat. No. 4,795,455, by S. Cadieux in E.P. Pat. No. 354,502, by A. T. Mays in E.P. Pat. No. 70,163, and by R. P. James in U.S. Pat. No. 4,368,323 (herein incorporated by reference) which are nonwovens made from hydrophobic fibers which have been coated with an adhesive or have been subjected to heat and/or pressure to fuse the individual fibers to each other. Such materials tend to provide only limited fluid absorption but serve to allow passage to lower layers for absorption and retention. As a result, the fluid is wicked away from the body, leaving the surface of the body-contacting layer feeling drier to the touch.

The use of hydrophobic fibers for the body contacting, or cover, layer allows fluid to pass through to the absorbent layers beneath yet does not retain moisture on the surface layer, thus providing greater comfort to the wearer by permitting her to feel dry for a longer period of time. The desirability of such a feature has been recognized by Levesque U.S. Pat. No. 3,838,692 (herein incorporated by reference) who describes a chemical method of providing porosity to hydrophobic materials.

The fluid-impermeable barrier layer 110 may be a nonwoven or woven fabric treated to become impervious to fluid. Typically, though, the barrier layer 110 is a plastic sheet composed of polyethylene or polypropylene. Such layers are taught, for example in U.S. Pat. No. 4,731,066 (Korpman).

The absorbent core 100 is, typically, a rectangular or hourglass shaped pad that is separate from the cover. The absorbent core 100 is preferably made from wood pulp or other cellulosic material. Such cores are taught, for example, in U.S. Pat. Nos. 4,552,618 (Kopolow) and 4,536,432 (Holtman) and in British patent no. 2,189705 (Mesek), incorporated herein by reference.

Additionally, the absorbent core 100 may utilize a variety of fluid immobilizing materials, e.g., superabsorbing polymers or peat moss, as a reservoir layer to increase fluid capacity or to minimize pad bulk. The reservoir layer may be made from cellulosic materials and, additionally, such materials as sphagnum peat moss and superabsorbent polymers which, gram for gram, absorb much greater quantities of fluid than pulp alone, allowing for the manufacture of much thinner absorbent pads. Typically, materials such as sphagnum and superabsorbent polymer are not used alone, but in conjunction with cellulosic pulp in order to provide extra absorbency for heavy fluid flow and to provide bulk to keep the product closer to the user's body. Such materials are taught by Y. Levesque in U.S. Pat. No. 4,507,122; S. Dabi in U.S. Pat. No. 4,494,963; by I. S. Ness in U.S. Pat. No. 4,880,419; by J. Roller in U.S. Pat. No. 4,443,492; hereby incorporated by reference.

When such fluid immobilizing materials are used, however, it has been found that while they have the ability to absorb many times their weight in body fluid, the rate of absorption is relatively slow. Thus, it is often preferred that a transfer layer 130 be incorporated into the absorbent core 100. The transfer layer 130 functions to draw fluid from the fluid permeable cover layer 90 and transport it to that portion of the core into which the bulk of the fluid will eventually be absorbed, often called the reservoir layer or absorbent core 100. Thus, placement of the transfer layer 130 in the absorbent product would be between the cover layer 90 and the reservoir layer 100. Typically, a transfer layer 130 functions to quickly absorb fluid and hold it until the slower absorbing reservoir layer 100 can accept it. Acceptable transfer layers 130 are those made from cellulosic materials, such as wood pulp, and an adhesive like binder. The basis weight of such materials would range from about 20–200 g/m$^2$. More preferably, they would range from about 50–150 g/m$^2$. Still more preferably, they would range from about 75–100 g/m$^2$. Still other suitable materials are discussed in U.S. patent application No. 08/075254, which is assigned to the same assignee of this application and herein incorporated by reference. Such materials, aside from those specifically disclosed in Ser. No. 08/075254, are well known in the art.

It is helpful for immediate accessibility of the fluid to the plates 10 and the spaces therebetween that the fluid that transfers through the intervening structures of cover 90, transfer layer 130, and reservoir layer 100 be obstructed as little as possible. One way to accomplish this is to create openings 50 through some or all of these structures that are large, even as large as those of the upper, lower, and (optional) intermediate plates 20,30,80. The openings 50 can be, but do not necessarily need to be in line with the openings 50 in the upper, lower, and (optional) intermediate plates 20,30,80.

Bulk layer 120 may be comprised of any absorbent or nonabsorbent material such as wood pulp fluff. Its purpose .it to give the napkin some bulk to allow it to better fit to the user's body. It is can also be used as a back-up absorbent source. But, as explained above its use as an absorbent layer is not absolutely necessary since the absorbent core is usually sufficient to absorb all fluid deposited on the napkin.

Sanitary napkins made by the teachings of this invention can be placed on the inner crotch portion of the user's underwear (not shown in the drawings) and kept in place by the use of adhesive (also not shown in the drawings). Such adhesives are well known in the art. Also, the drawings show the use of attachment tabs. But, such tabs are optional.

An alternative way of manufacturing a sanitary napkin (not shown in the drawings), according to the teachings of this invention, involve placing the upper and lower plates 20,30 between the absorbent core 100 and the cover layer 90, wherein the upper plate 20 is adjacent the cover layer 90 and the lower plate is adjacent the absorbent core 100. In this way fluid will continually flow down toward the absorbent core 100. In such an embodiment, the lower plate 30 should have openings to permit fluid to flow through it to the absorbent core 100. Alternatively, the lower plate 30 can be without openings if it is small enough in area to permit fluid to flow over and around it to the absorbent core 100. Further, if the absorbent core 100 has sufficient strength, it may be possible to eliminate the lower plate 30 altogether and, instead, have the upper plate 20 and spacers 40 rest on the upper surface of the absorbent core 100.

EXAMPLE

In order to demonstrate the effect of gap distance between an upper and a lower plate, the following experiment was performed. Two plates of polycarbonate sold under the trademark Lexan®, each with the dimensions 12"x4"x0.5", were obtained Into the top plate was drilled a 0.5" hole. Shims were placed between each plate to create a gap which varied from 0.012" to 0.125".

Two types of synthetic menstrual fluid, SMF1 and SMF2, were prepared. The low viscosity fluid, SMF1, is formulated with physical properties (surface tension, viscosity, specific gravity, etc.) consistent with that of whole blood. The high viscosity fluid, SMF2, is formulated with a viscosity that is much greater than that of whole blood and represents the very viscous, gelatinous material common to menstrual discharges. SMF1 and SMF2 were prepared by dissolving 0.15% and 0.4% poly acrylamide, respectively, in isotonic phosphate buffer (pH 7.4). Approximately 0.3% Germabean was added to prevent bacterial growth. The viscosity of SMF1 and SMF2 was measured at 30 cps and 280 cps, respectively.

The plates were positioned with the upper plate over the lower plate. Seven (7) cc of SMF1 was poured through the hole and the time recorded when the fluid reached each of three different states: (1) "level off"; (2) "halo"; and (3) dry spot. "Level off" is the time for the fluid to reach from the bottom to the top of the gap between the plates. "Halo" is the time for the fluid to flow away from the fluid inlet creating a 0.25" diameter circle on the top surface of the bottom plate. "Dry spot" is the time taken to form a dry spot on the top surface of the bottom plate.

Figure 7:
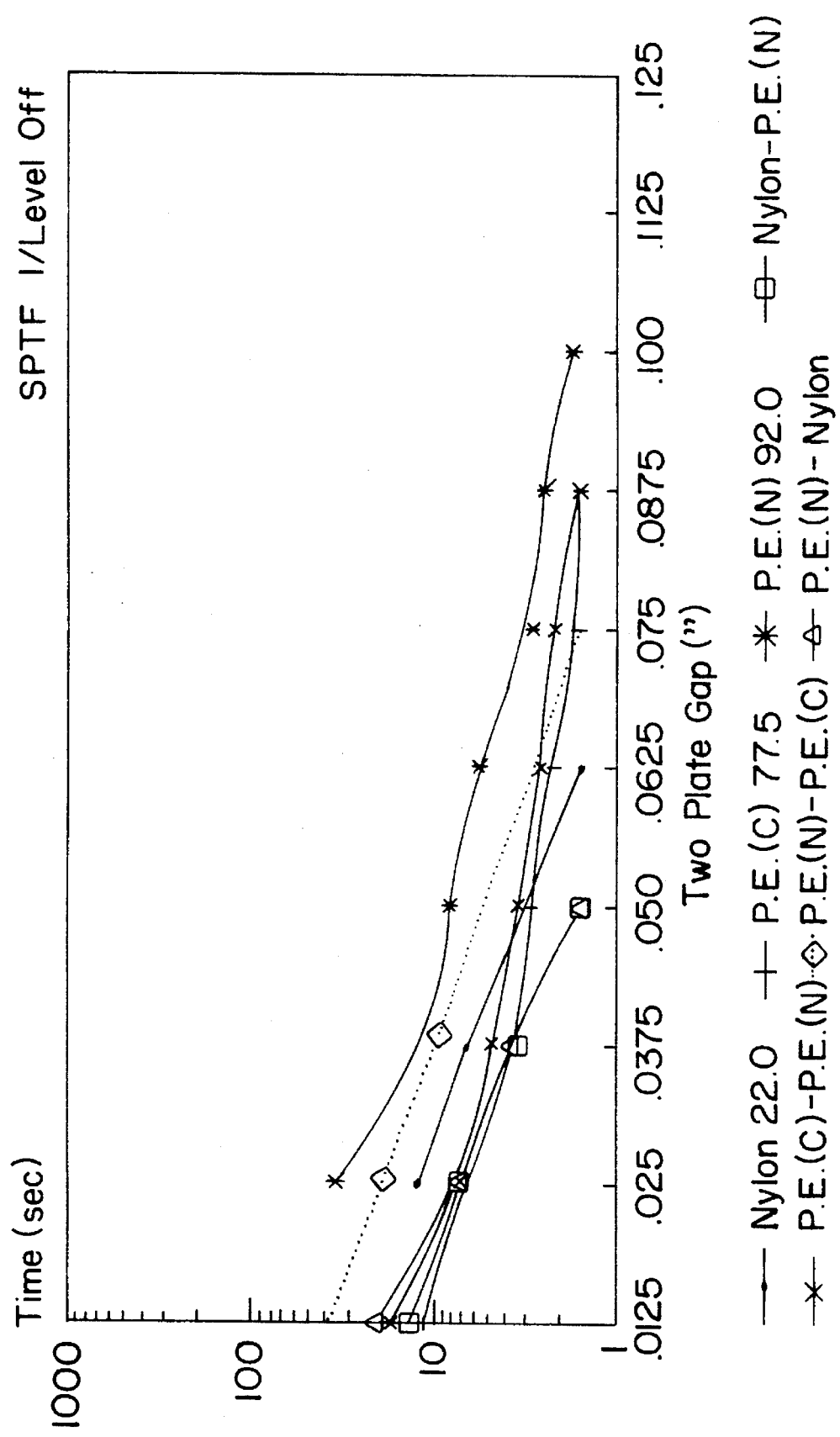
Figure 8:
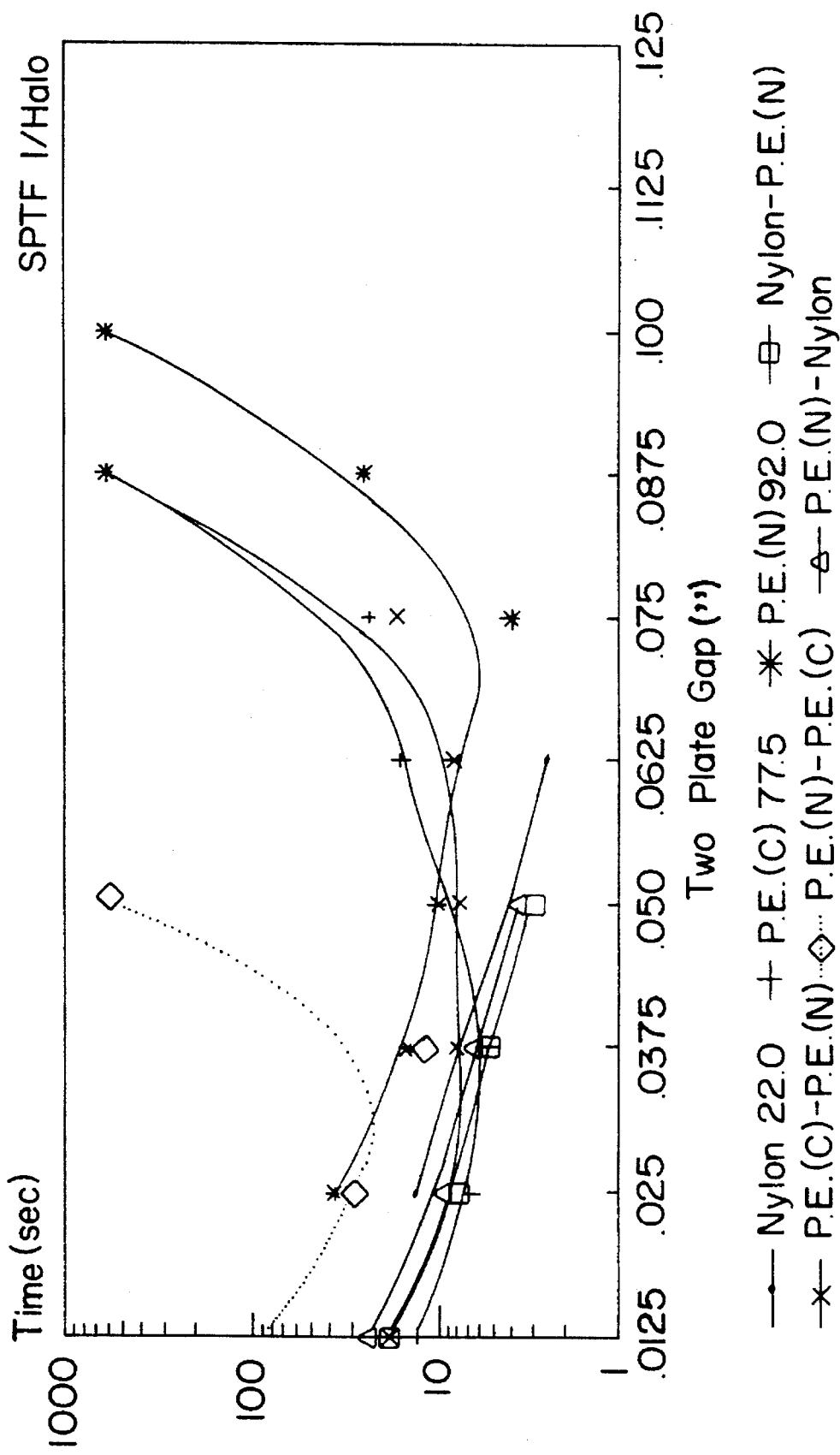
Figure 9:
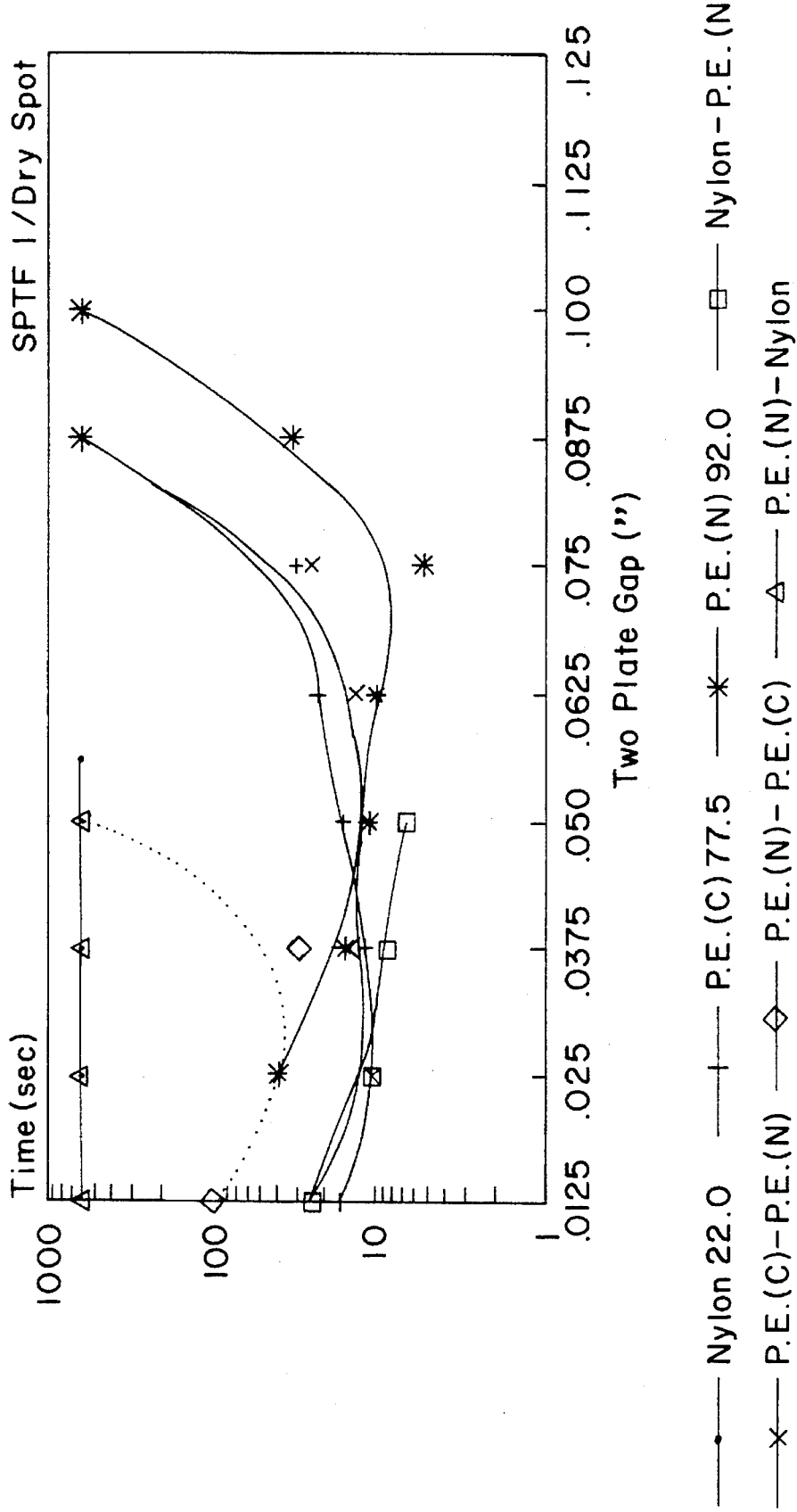

This test described above was conducted a number of times, with the lower surface of the upper plate and the top surface of the lower plate modified by attaching a thin film of the following wettable materials: (1) nylon with 22 degrees of contact angle with SMF1 and polyethylene both with and without corona treatment. The results of the testing are graphically shown in FIGS. 7 through 9.

In interpreting these graphs, the following definitions apply:

"Nylon 22" means that both the upper surface of the lower plate and lower surface of the upper plate are covered by wettable nylon film having 22 degrees of contact angle with SMF1.

"P.E.(C) 77.5" means that both the upper surface of the lower plate and lower surface of the upper plate are covered by polyethylene film with Corona treatment and having 77.5 degrees of contact angle with SMF1.

"P.E.(N) 92.0" means that both the upper surface of the lower plate and lower surface of the upper plate are covered by polyethylene film without Corona treatment and having 92 degrees of contact angle with SMF1.

"Nylon-P.E.(N)" means that a nylon film having 22 degrees of contact with SMF1 is applied to the lower surface of the upper plate and PE film without Corona treatment and having 92 degrees of contact angle with SMF1 when it is applied to the upper surface of the lower plate.

"P.E.(C)-P.E.(N)" means that a PE film with Corona treatment and having 77.5 degrees of contact with SMF1 when it is applied to the lower surface of the upper plate and PE film without Corona treatment and having 92 degrees of contact with SMF1 when it is applied to the upper surface of the lower plate.

"P.E.(N)-P.E.(C)" means that a PE film without Corona treatment having 92 degrees of contact with SMF1 is applied to the lower surface of the upper plate and PE film with Corona treatment having 77.5 degrees of contact with SMF1 is applied to the upper surface of the lower plate.

"P.E.(N)-Nylon" means that PE film without Corona treatment and having 92 degrees of contact angle with SMF1 when it is applied to the lower surface of the upper plate and a nylon film having 22 degrees of contact with SMF1 when it is applied to the upper surface of the lower plate.

Figure 10:
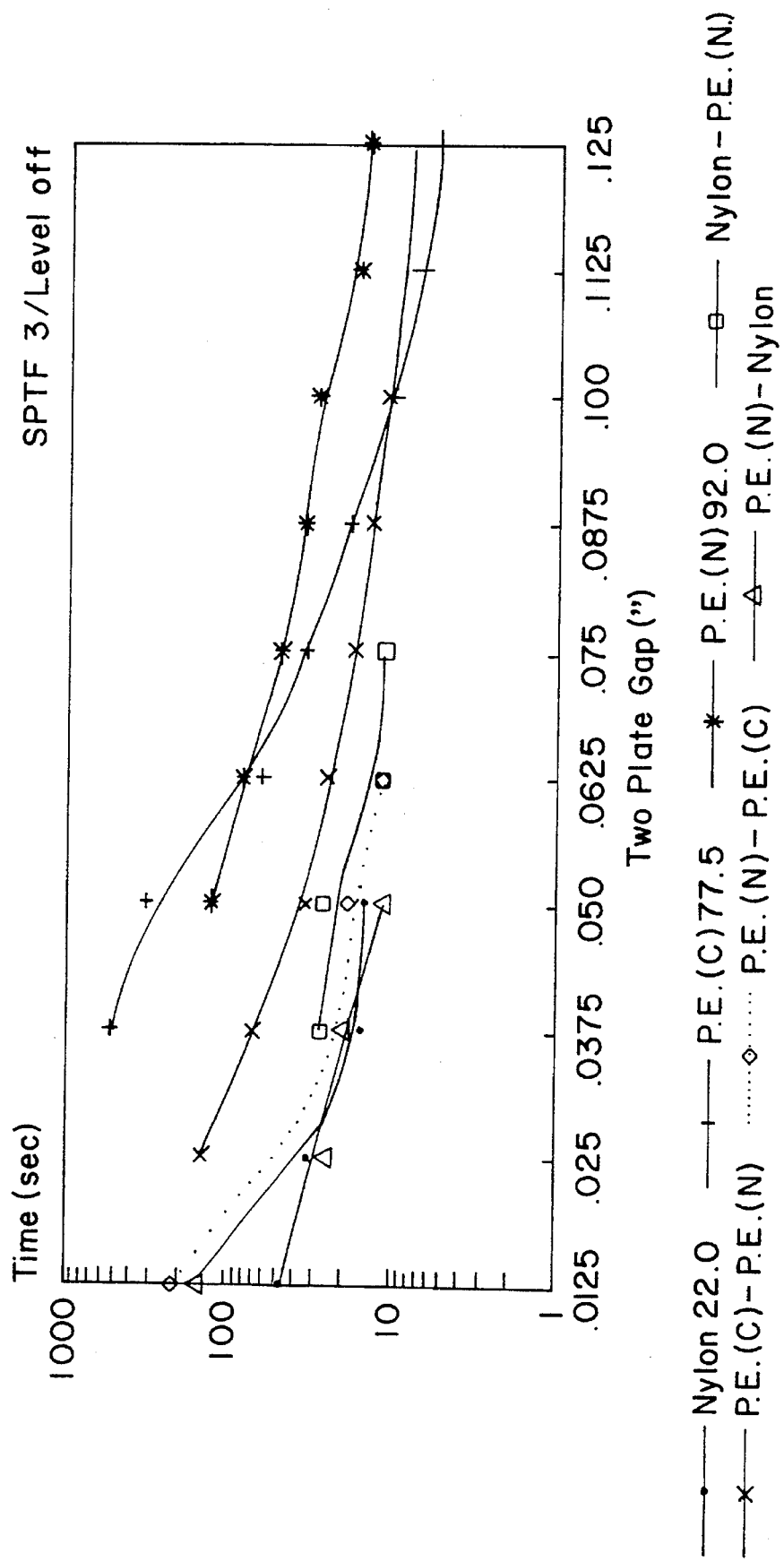

The test was then repeated using SMF2 as the test fluid. The results are graphically shown in FIGS. 10 through 12.

We claim:

1. An absorbent product comprising an upper plate and a lower plate which are spaced apart from each other, and wherein a plurality of openings extend through the upper plate and further comprising an intermediate plate positioned between and spaced apart from the upper and lower plates by means of spacer elements to maintain an open area therebetween, wherein the intermediate plate has a plurality of openings extending through said intermediate plate.

2. The absorbent product of claim 1 wherein at least one surface of the plates is wettable.

3. The absorbent product of claim 2 wherein the wettable surface is on a surface of the lower plate.

4. The absorbent product of claim 1 wherein the upper plate has a top surface area and the openings take up from about 0.01 to about 8 square inches of the top surface area.

5. The absorbent product of claim 4 wherein the upper plate has a bottom surface area and the openings take up from about 0.01 to about 8 square inches of the bottom surface area.

6. The absorbent product of claim 5 wherein the bottom surface area taken up by openings is less than the top surface area taken up by openings.

7. The absorbent product of claim 1 wherein the upper and intermediate plates each have a top surface area and the openings take up from about 0.01 to about 8 square inches of the top surface area.

8. The absorbent product of claim 7 wherein the upper and intermediate plates each have a bottom surface area the openings take up from about 0.01 to about 8 square inches of the bottom surface area.

9. The absorbent product of claim 8 wherein the bottom surface area taken up by openings of each of the upper and intermediate plates is less than the top surface area taken up by openings of each of the upper and intermediate plates.

10. An absorbent product comprising:

a fluid permeable cover layer;

an absorbent core;

a fluid impermeable barrier layer; and two plates, comprising an upper plate and a lower plate, positioned between the barrier layer and the absorbent core, wherein the upper plate is adjacent the absorbent core and the lower plate is adjacent the barrier layer, wherein the plates are spaced apart from each other by means of spacer elements to maintain an open area therebetween, and wherein a plurality of openings extend through the upper plate.

11. The absorbent product of claim 10 further comprising an absorbent layer positioned between the barrier layer and the lower plate.

12. The absorbent product of claim 10 wherein the absorbent core comprises peat moss.

13. The absorbent product of claim 12 wherein the absorbent core further comprises a transfer layer positioned between the peat moss layer and the cover layer.

14. The absorbent product of claim 11 wherein the absorbent core comprises peat moss and the absorbent layer comprises wood pulp fluff.

15. The absorbent product of claim 14 wherein the openings extend through the cover layer and the absorbent core.

16. An absorbent product comprising:

a fluid permeable cover layer;

an absorbent core;

a fluid impermeable barrier layer; and two plates, comprising an upper plate and a lower plate, positioned between the absorbent core and the cover layer, wherein the upper plate is adjacent the cover layer and the lower plate is adjacent the absorbent core, wherein the plates are spaced apart from each other by means of spacer elements to maintain an open area therebetween, and wherein a plurality of openings extend through the upper plate.

17. The absorbent product of claim 16 wherein the absorbent core comprises peat moss.

18. The absorbent product of claim 17 wherein the absorbent core further comprises a transfer layer positioned between the peat moss layer and the cover layer.

19. The absorbent product of claim 16 wherein the openings extend through the cover layer.

* * * * *